United States Patent
Wang

(10) Patent No.: US 7,746,464 B2
(45) Date of Patent: Jun. 29, 2010

(54) INSPECTION DEVICE AND METHOD FOR INSPECTING COATED TRANSPARENT COMPONENT

(75) Inventor: Chung-Pei Wang, Taipei Hsien (TW)

(73) Assignee: Hon Hai Precision Industry Co., Ltd., Tu-Cheng, Taipei Hsien (TW)

(*) Notice: Subject to any disclaimer, the term of this patent is extended or adjusted under 35 U.S.C. 154(b) by 24 days.

(21) Appl. No.: 12/273,704

(22) Filed: Nov. 19, 2008

(65) Prior Publication Data

US 2009/0279078 A1 Nov. 12, 2009

(30) Foreign Application Priority Data

May 9, 2008 (CN) .......................... 2008 1 0301523

(51) Int. Cl.
*G01N 21/00* (2006.01)
(52) U.S. Cl. .................. 356/239.1; 118/712; 427/8
(58) Field of Classification Search ... 356/237.1–237.5, 356/239.1–239.4, 429–431; 118/665, 712, 118/668, 52, 620, 666; 427/8–10, 240, 444; 250/559.45
See application file for complete search history.

(56) References Cited

U.S. PATENT DOCUMENTS

| 5,066,132 A * | 11/1991 | Nagata et al. ............... 356/432 |
| 5,691,811 A * | 11/1997 | Kihira ..................... 356/239.1 |
| 6,011,620 A * | 1/2000 | Sites et al. ............... 356/239.1 |
| 6,927,408 B2 * | 8/2005 | Onishi et al. ........... 250/559.45 |
| 7,133,126 B2 * | 11/2006 | Van Steenkiste et al. . 356/237.1 |
| 2004/0179193 A1* | 9/2004 | Maezono et al. ......... 356/239.1 |
| 2006/0203246 A1* | 9/2006 | Nakajima et al. ........... 356/430 |

* cited by examiner

*Primary Examiner*—Hoa Q Pham
(74) *Attorney, Agent, or Firm*—Clifford O. Chi

(57) ABSTRACT

A inspection device for inspecting coated transparent components includes an opaque container, a light source and a light intensity detector. The opaque container has a first end and a second end opposite to the first end. A retaining portion is formed in the opaque container and positioned between the first and second ends and configured to retain the coated transparent components. The light source is positioned on the first end and configured to emit light passing through the coated transparent components. The light intensity detector is positioned on the second end and configured to detect the intensity of light transmitted through the coated transparent components to the light intensity detector, and calculate a light transmission rate.

20 Claims, 3 Drawing Sheets

INSPECTION DEVICE AND METHOD FOR INSPECTING COATED TRANSPARENT COMPONENT

BACKGROUND

1. Technical Field

The present disclosure relates to an inspection device and a method for inspecting coated transparent component.

2. Description of Related Art

Transparent components are generally coated with a film. Defects often occur on the film, therefore the coated transparent components must be inspected to ensure quality. Typically quality controlled is accomplished by visual inspection to inspect the coated transparent components. However, the visual inspection has a low efficiency and accuracy, and can not meet the demands of mass production.

Therefore, a new device and method for inspecting coated transparent component is desired to overcome the above-described shortcomings.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION OF THE EMBODIMENTS

Figure 1:
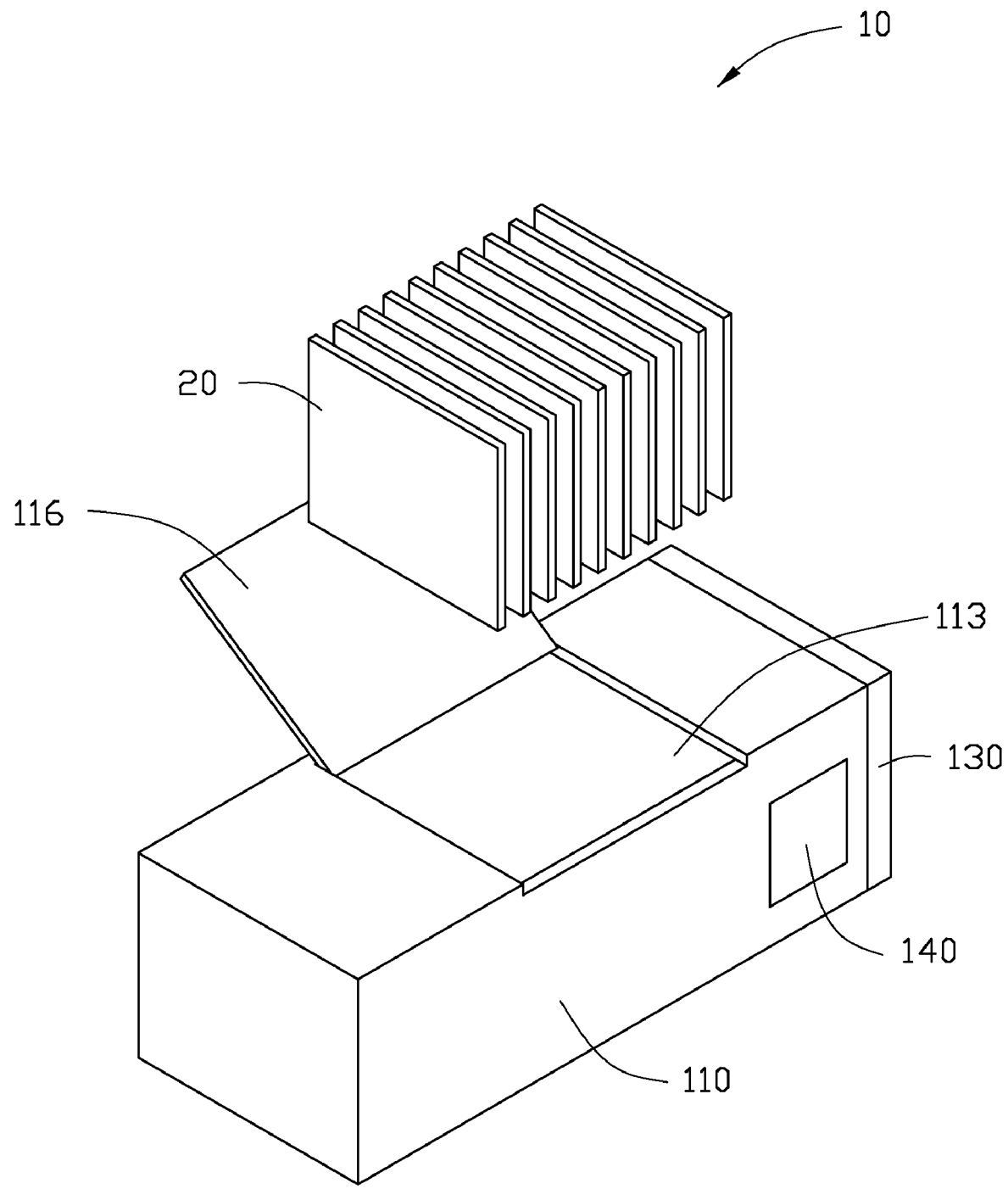
FIG. 1 is a perspective view of one embodiment of an inspection device for inspecting coated transparent components.
Figure 2:
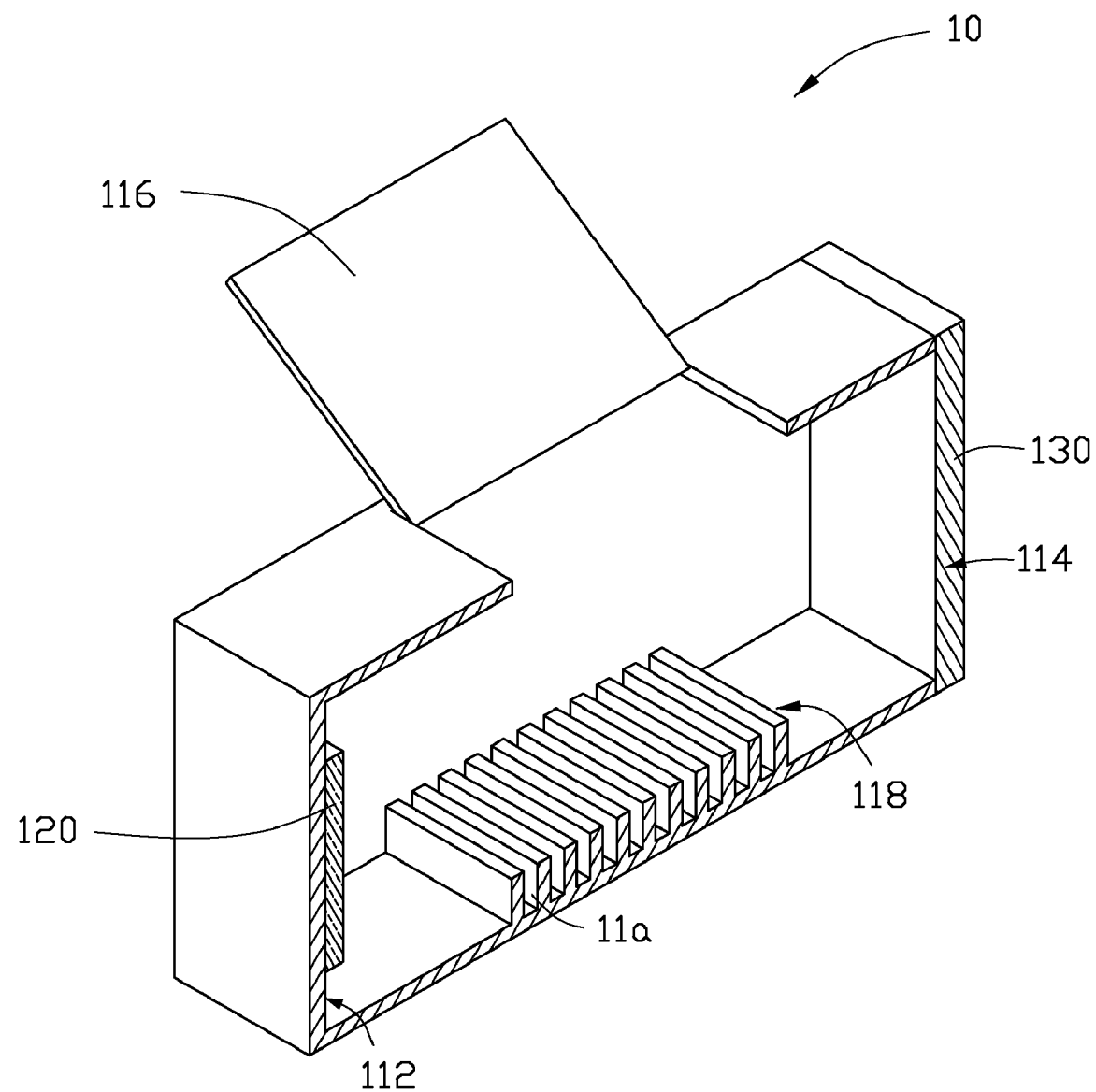
FIG. 2 is a cross-sectional view of the inspection device of FIG. 1.

Referring to FIGS. 1 and 2, one embodiment of an inspection device 10 for inspecting a plurality of coated transparent components 20 includes an opaque container 110, a light source 120, a light intensity detector 130, and a display component 140.

The opaque container 110 may be rectangular shaped and has a first end 112 and a second end 114 opposite and parallel to the first end 112. A retaining portion 118 is positioned in the opaque container 110 between the first and second ends 112, 114. A plurality of spaced grooves 11a is defined in the retaining portion 118 and configured to receive the coated transparent components 20. In one embodiment, the spaced grooves 11a may be rectangular shaped and arranged parallel to the first and second ends 112, 114. Each coated transparent component 20 may be a coated transparent substrate. An opening 113 is defined in the opaque container 110 opposite to the retaining portion 118. A door 116 may be rotatably secured on the opaque container 110 and configured to cover and expose the opening 113.

The light source 120 is positioned on the first end 112 and configured to emit light to pass through the coated transparent components 20. In one embodiment, the light source 120 may be a plane light source.

The light intensity detector 130 is positioned on the second end 114 and configured to detect the intensity of light transmitted through the coated transparent components 20 to the light intensity detector 130, and calculate a light transmission rate. The light transmission rate is a ratio of the intensity of the light transmitted through the coated transparent components 20 to the intensity of the light not transmitted through the coated transparent components 20. The intensity of the light not transmitted through the coated transparent components 20 is pre-stored in the light intensity detector 130. In one embodiment, the light intensity detector 130 may be a photometer.

The display component 140 is electrically coupled to the light intensity detector 130, secured on the opaque container 110, and configured to display the light transmission rate. In one embodiment, the display component 140 may be a liquid crystal display component.

The coated transparent components 20 are delivered in the opaque container 110 through the opening 113 and positioned in the spaced grooves 11a. The coated transparent components 20 are positioned parallel to the first and second ends 112, 114. The door 116 is closed to cover the opening 113. The light source 120 is turned on to emit the light. The light passes through the plurality of coated transparent components 20 and arrives at the light intensity detector 130. The light intensity detector 130 detects the transmitted light to obtain the light intensity. The light transmission rate is calculated by the light intensity detector 130 and delivered to the display component 140. The display component 140 displays the light transmission rate. The light transmission rate can be used as a parameter to assess the quality of the plurality of coated transparent components 20. In one embodiment, if the light transmission rate is greater than or equal to a predetermined light transmission rate, for example 90%, the plurality of coated transparent components 20 meets the requirement of quality.

Figure 3:
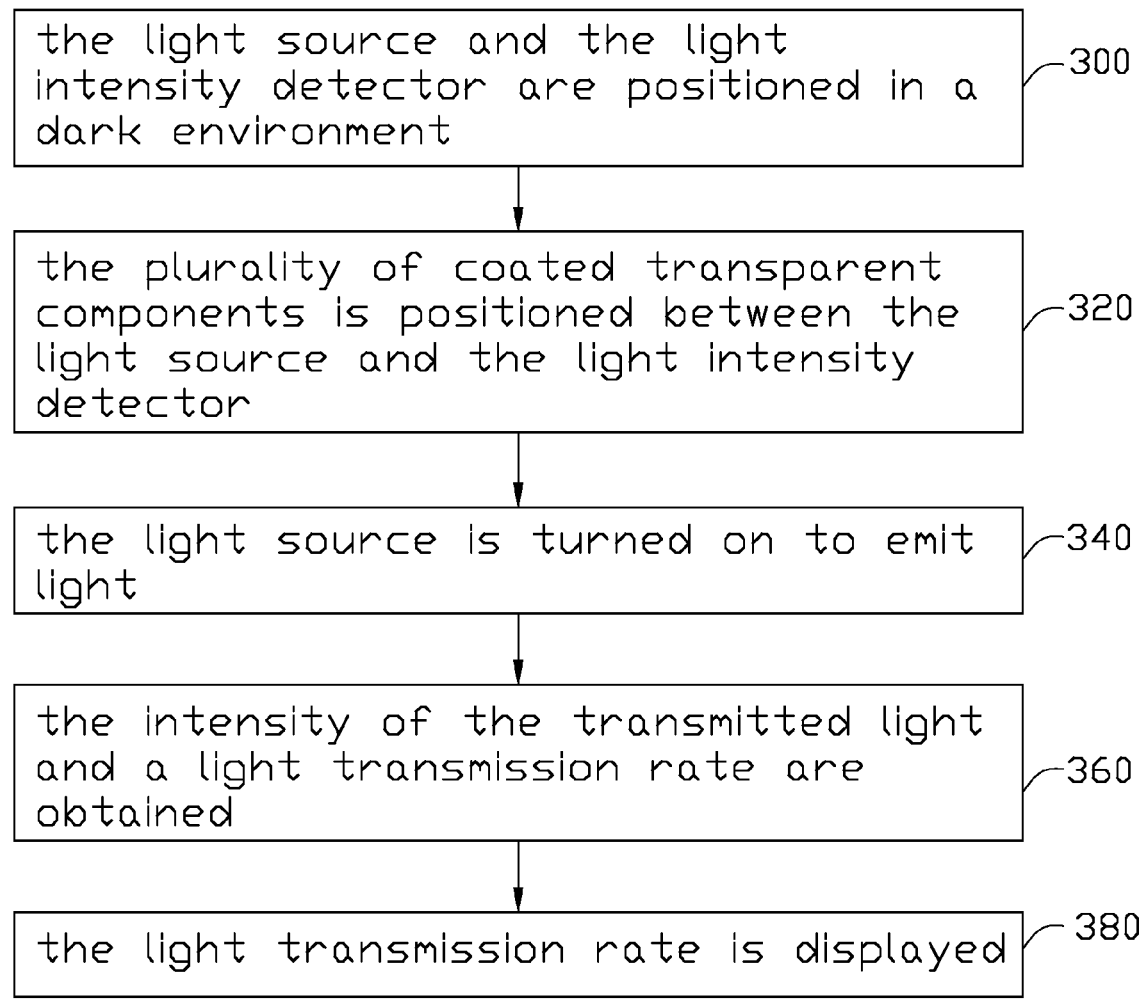
FIG. 3 is a flowchart of one embodiment of a method for inspecting coated transparent component.

Referring to FIG. 3, one embodiment of a method for inspecting the plurality of coated transparent components 20 is provided. Depending on the embodiment, certain of the steps described below may be removed, others may be added, and the sequence of steps may be altered.

In step 300, the light source 120 and the light intensity detector 130 are positioned in a dark environment, such as the opaque container 110.

In step 320, the plurality of coated transparent components 20 is positioned between the light source 120 and the light intensity detector 130. In one embodiment, the coated transparent components 20 are positioned substantially perpendicular to the light path between the light source 120 and the light intensity detector 130.

Continuing to step 340, the light source 120 is turned on to emit light. The light perpendicularly passes through the coated transparent components 20 to the light intensity detector 130.

Still continuing to step 360, the intensity of the transmitted light and a light transmission rate are obtained. The light intensity detector 130 detects the intensity of the transmitted light and calculates the light transmission rate.

Moving to step 380, the light transmission rate is displayed. The light transmission rate is delivered to and displayed by the display component 140.

It is believed that the present embodiments and their advantages will be understood from the foregoing description, and it will be apparent that various changes may be made thereto without departing from the spirit and scope of the embodiments or sacrificing all of its material advantages, the examples here before described merely being preferred or exemplary embodiments.

What is claimed is:

1. An inspection device for inspecting a plurality of coated transparent components, comprising:
   an opaque container having a first end and a second end opposite to the first end;
   a retaining portion positioned in the opaque container between the first and second ends and configured to retain the coated transparent components;
   a light source positioned on the first end and configured to emit light to pass through the coated transparent components; and
   a light intensity detector positioned on the second end and configured to detect the intensity of light transmitted through the coated transparent components to the light intensity detector, and calculate a light transmission rate.

2. The inspection device of claim 1, further comprising a display component electrically coupled to the light intensity detector and configured to receive and display the light transmission rate.

3. The inspection device of claim 2, wherein the display component is a liquid crystal display component.

4. The inspection device of claim 1, wherein the opaque container is rectangular shaped.

5. The inspection device of claim 1, wherein a plurality of spaced grooves is defined in the retaining portion and configured to receive the coated transparent components.

6. The inspection device of claim 5, wherein the plurality of spaced grooves is rectangular shaped and positioned parallel to the first and second ends.

7. The inspection device of claim 1, wherein an opening is defined in the opaque container opposite to the retaining portion.

8. The inspection device of claim 7, where a door is rotatably secured on the opaque container and configured to cover and expose the opening.

9. The inspection device of claim 1, wherein the light source is a plane light source.

10. The inspection device of claim 1, wherein the light intensity detector is a photometer.

11. The inspection device of claim 1, wherein the light intensity of the light not transmitted through the coated transparent components is pre-stored in the light intensity detector.

12. A method for inspecting a plurality of coated transparent components, comprising:
    positioning a light source and a light intensity detector in a dark environment;
    positioning the coated transparent components between the light source and the light intensity detector;
    turning on the light source to emit light, wherein the light passes through the coated transparent components to the light intensity detector; and
    obtaining the intensity of light transmitted through the coated transparent components to the light intensity detector, and a light transmission rate via the light intensity detector.

13. The method of claim 12, wherein the dark environment is an opaque container having a first end and a second end opposite to the first end; a retaining portion is positioned in the opaque container; the light source is positioned on the first end; the light intensity detector is positioned on the second end; the coated transparent components is positioned in the retaining portion.

14. The method of claim 13, wherein the opaque container is rectangular shaped.

15. The method of claim 14, wherein a plurality of spaced grooves is defined in the retaining portion and receives the coated transparent components.

16. The method of claim 15, wherein the spaced grooves is rectangular shaped and positioned parallel to the first and second ends.

17. The method of claim 12, wherein the light source is a plane light source.

18. The method of claim 12, wherein the light perpendicularly passes through the coated transparent components.

19. The method of claim 12, wherein the intensity of the light not transmitted through the coated transparent components is pre-stored in the light intensity detector.

20. The method of claim 12, further comprising displaying the light transmission rate on a display component.

* * * * *